United States Patent [19]

Kumai et al.

[11] Patent Number: 4,985,588
[45] Date of Patent: Jan. 15, 1991

[54] NUCLEUS-FLUORINATED AROMATIC CARBOXYLATES AND PROCESSES FOR THEIR PRODUCTION

[75] Inventors: Seisaku Kumai, Fujisawa; Osamu Yokokouji, Yokohama, both of Japan

[73] Assignee: Asahi Glass Company Ltd., Tokyo, Japan

[21] Appl. No.: 405,430

[22] Filed: Aug. 28, 1989

[30] Foreign Application Priority Data

Aug. 26, 1988 [JP] Japan .................. 63-210803

[51] Int. Cl.$^5$ ............................................. C07C 69/76
[52] U.S. Cl. ..................................... 560/103; 560/83; 560/106; 560/111
[58] Field of Search ................. 560/103, 83, 106, 111

[56] References Cited

FOREIGN PATENT DOCUMENTS 3131735 3/1983 Fed. Rep. of Germany .
3426483 1/1986 Fed. Rep. of Germany .
3529259 2/1987 Fed. Rep. of Germany .

OTHER PUBLICATIONS

CA84(11):73784d, 1975.

Primary Examiner—Paul J. Killos
Attorney, Agent, or Firm—Oblon, Spivak, McClelland, Maier & Neustadt

[57] ABSTRACT

A process for producing nucleus-fluorinated aromatic carboxylates, which comprise nucleus-fluorinating aromatic carboxylates of the following formula (1) with a fluorinating agent to obtain nucleus-fluorinated aromatic carboxylates of the following formula (2):

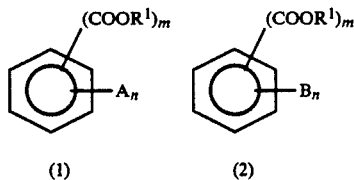

wherein $R^1$ is an alkyl group, an aryl group or a fluoroalkyl group, each of A and B is at least one member selected from the group consisting of a hydrogen atom, a halogen atom, an alkyl group, an aryl group and a fluoroalkyl group, and n and m are integers satisfying $m+n=6$, provided that m is 1 or 2, provided that at least one A is an activated chlorine or bromine atom, and B corresponding to such an activated chlorine or bromine atom is a fluorine atom.

18 Claims, No Drawings

NUCLEUS-FLUORINATED AROMATIC CARBOXYLATES AND PROCESSES FOR THEIR PRODUCTION

The present invention relates to nucleus-fluorinated aromatic carboxylates useful as intermediates for pharmaceuticals or for agricultural chemicals, particularly for antimicrobial agents, and processes for their production.

When a halogen atom on a benzene ring is to be substituted by a fluorine atom by a reaction with a fluorinating agent such as an alkali metal fluoride, an electron withdrawing group is usually required to be present at the o- or p-position to the halogen atom. Heretofore, it has been known to use as such an electron withdrawing group, a nitro group (—NO$_2$) (e.g. Japanese Unexamined Patent Publication No. 111020/1978), a cyano group (—CN) (e.g. Japanese Unexamined Patent Publication No. 189151/1983) or a chloroformyl group (—COCl) (e.g. Japanese Unexamined Patent Publication No. 1667/1986). However, no instances have been known wherein an alkoxy carbonyl group (—COOR) or an aryloxy carbonyl group (—COOR) is used as such an electron withdrawing group.

Further, it is considered possible to obtain a nucleus-fluorinated aromatic carboxylate by a proper combination of conventional techniques. For example, in a case of the nucleus-fluorinated benzoate, the following processes are conceivable.

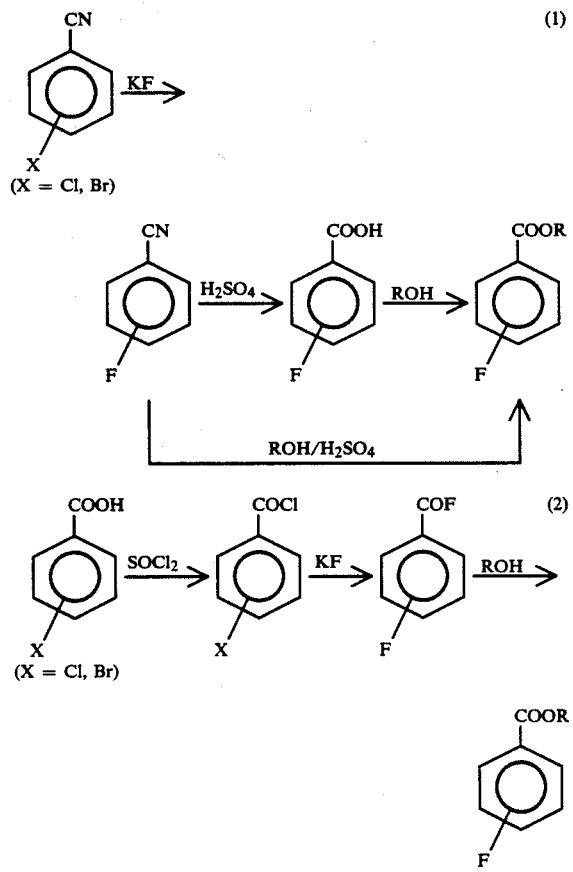

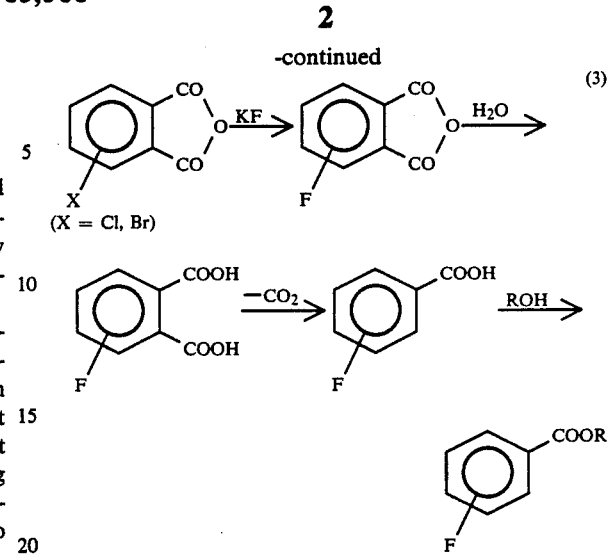

Namely, there are a method (1) wherein a halogenated benzonitrile compound is fluorinated by KF (Japanese Unexamined Patent Publication No. 189151/1983), followed by. hydrolysis and esterification, a method (2) wherein a halogenated benzoic acid compound is converted to a benzoyl chloride compound, which is then fluorinated (Japanese Unexamined Patent Publication No. 1667/1986), followed by the reaction with an alcohol or a phenol to obtain a nucleus-fluorinated benzoate, and a method (3) wherein a halogenated phthalic anhydride is fluorinated by KF (J. Chem. Soc., 1964, 1194 (1964)), followed by hydrolysis, decarboxylation and esterification.

In the method (1) wherein a halogenated benzonitrile compound is used as the starting material, the starting material is relatively expensive, and depending upon the compound, the material is hardly available.

The method (2) wherein a halogenated benzoic acid compound is used as the starting material, requires three steps, and it is necessary to employ a dehydrated and dried benzoic acid compound, since the acid chloride reaction is required to be conducted in the absence of water. Further, when thionyl chloride is used as a reaction reagent for this reaction, poisonous sulfur dioxide gas (SO$_2$) is produced in a large amount as a by-product. Besides, the resulting benzoyl chloride compound is unstable against water, and a due care is required for its handling. In addition, it is necessary to conduct dehydration of the solvent and the fluorinating agent sufficiently also for the fluorination of the benzoyl chloride compound. Thus, this method is cumbersome and not desirable.

By the method (3) wherein a halogenated phthalic anhydride is used as the starting material, many steps are required, and it is impossible to obtain a compound like a 2,6-difluorobenzoate. Thus, compounds producible by this method are limited. Besides, if a tetrachlorophthalic anhydride is fluorinated with KF, the desired tetrafluorophthalic anhydride can not be obtained, and the product is reported to be octafluoroanthraquinone.

It is an object of the present invention to shorten the conventional multi-step reaction and to overcome the cumbersomeness of the process.

The present invention provides a process for producing nucleus-fluorinated aromatic carboxylates, which comprises nucleus-fluorinating aromatic carboxylates of the following formula (1) with fluorinating agents to obtain nucleus-fluorinated aromatic carboxylates of the following formula (2):

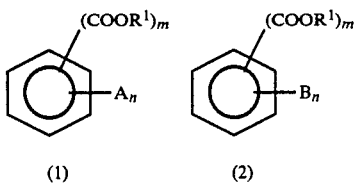

wherein $R^1$ is an alkyl group, an aryl group or a fluoroalkyl group, each of A and B is at least one member selected from the group consisting of a hydrogen atom, a halogen atom, an alkyl group, an aryl group and a fluoroalkyl group, and n and m are integers satisfying $m+n=6$, provided that m is 1 or 2, provided that at least one A is an activated chlorine or bromine atom, and B corresponding to such an activated chlorine or bromine atom is a fluorine atom.

The process of the present invention has a feature that inexpensive and readily available halogenated aromatic carboxylates are reacted with fluorinating agents such as an alkali metal fluoride to obtain nucleus-fluorinated aromatic carboxylates. The starting material carboxylates may be obtained by esterification of inexpensive halogenated aromatic carboxylic acids. By the process of the present invention, the nucleus-fluorinated aromatic carboxylates can be produced in good yield at a low cost. Further, the process of the present invention is efficient without a cumbersome step such as a step of dehydration of a solid which used to be required by the combination of the conventional techniques.

Now, the present invention will be described in detail with reference to the preferred embodiments.

In the formulas (1) and (2), the alkyl group and the fluoroalkyl group (i.e. an alkyl group with the hydrogen atoms partially or entirely substituted by fluorine atoms which may, in turn, partially substituted by chlorine or bromine atoms) preferably have from 1 to 20 carbon atoms, and the aryl group may have a substituent such as a halogen atom or an alkyl group. The halogen atom for A or B includes a chlorine atom, a fluorine atom and a bromine atom, and at least one A is an activated chlorine or bromine atom. B corresponding to such an activated chlorine or bromine atom is a fluorine atom.

The chlorine or bromine atom for A is activated by —$COOR^1$ in the formula. A chlorine or bromine atom located at the o- or p-position to —$COOR^1$ is particularly activated. By changing the type of $R^1$, the chlorine or bromine atom at the o- or p-position only, or at both the o- and p-position can be activated. The activated chlorine or bromine atom is substituted by a fluorine atom by the nucleus-fluorination. On the other hand, when $m=2$ in the formula and the rest of A are all chlorine or bromine atoms, the chlorine or bromine atom at the m-position to —$COOR^1$ will also be activated, and such a chlorine or bromine atom will be substituted by a fluorine atom by the nucleus-fluorination.

Specific examples of the aromatic carboxylates of the formula (1) include 2,2,2-trifluoroethyl 2-chlorobenzoate, ethyl 4-chlorobenzoate, isopropyl 4-chlorobenzoate, 2,2,2-trifluoroethyl 2,4-dichlorobenzoate, 2,2,2-trifluoroethyl 2,4-dichloro-5-tetrafluorobenzoate, methyl 2,4-dichlorobenzoate, isopropyl 2,4-dichlorobenzoate, 2,2,2-trifluoroethyl 2',6'-dichlorobenzoate, ethyl 2,6-dichlorobenzoate, isopropyl 2,6-dichlorobenzoate, methyl 2,4,6-trichlorobenzoate, methyl 2,4-dichloro-5-fluorobenzoate, ethyl 2,4-dichloro-5-fluorobenzoate, n-propyl 2,4-dichloro-5-fluorobenzoate, isopropyl 2,4-dichloro-5-fluorobenzoate, butyl 2,4-dichloro-5-fluorobenzoate, isobutyl 2,4-dichloro-5-fluorobenzoate, cyclohexyl 2,4-dichloro-5-fluorobenzoate, phenyl 2,4-dichloro-5-fluorobenzoate, 2,2,2-trifluoroethyl 2',4'-dichloro-5'-fluorobenzoate, dimethyl tetrachlorophthalate, bis(2,2,2-trifluoroethyl) tetrachlorophthalate, and these compounds with their chlorine atoms partially or entirely substituted by bromine atoms.

The reaction to substitute a fluorine atom for the chlorine or bromine atom on the benzene ring of the aromatic carboxylate can be conducted by reacting the aromatic carboxylate with a fluorinating agent in the absence or presence of an aprotic solvent. The fluorinating agent is preferably an alkali metal fluoride such as NaF, KF, RbF or CsF. Particularly preferred is spray-dried potassium fluoride. The fluorinating agent is employed in an amount of from 1 to 5 mols, preferably from 1 to 2 mols per mole of the halogen atom to be substituted. For the fluorination, a phase transfer catalyst may be added as an accelerator for the reaction. As such phase transfer catalysts, quaternary ammonium salts such as tetramethyl ammonium chloride or tetrabutyl ammonium bromide, or quaternary phosphonium salts such as tetrabutyl phosphonium bromide or tetraphenyl phosphonium bromide, may be mentioned. As the aprotic solvent, N,N-dimethylformamide, N,N-dimethylacetamide, dimethylsulfoxide, dimethylsulfone, sulfolane hexamethylphosphorotriamide, N-methyl-2-pyrrolidone, acetonitrile, benzonitrile, dioxane, diglyme or tetraglyme may be employed. However, preferred is sulfolane or N,N-dimethylformamide. The solvent is used usually in an amount of from the same amount to 10 times by weight, preferably from 2 to 5 times by weight, relative to the starting material. The reaction is conducted usually under atmospheric pressure or under an elevated pressure at a reaction temperature of from 50° to 250° C., preferably from 100° to 230° C. Among the compounds of the formulas (1) and (2), preferred are 2,4-dichloro-5-fluorobenzoates of the following formula (3) and 2-chloro-4,5-difluorobenzoates of the following formula (4), respectively. These compounds are novel compounds.

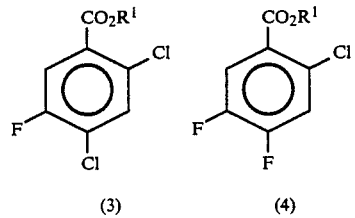

wherein $R^1$ is an alkyl group, an aryl group or a fluoroalkyl group. The compounds of the formula (3) include, for example, isopropyl 2,4-dichloro-5-fluorobenzoate, n-propyl 2,4-dichloro-5-fluorobenzoate, butyl 2,4-dichloro-5-fluorobenzoate, isobutyl 2,4-dichloro-5-fluorobenzoate, cyclohexyl 2,4-dichloro-5-fluorobenzoate and 2,2,2-trifluoroethyl-2,4-dichloro-5-fluorobenzoate. Likewise, the compounds of the formula (4) include methyl 2-chloro-4,5-difluorobenzoate, ethyl 2-chloro-4,5-difluorobenzoate, n-propyl 2-chloro-4,5-difluorobenzoate, isopropyl 2-chloro-4,5-difluorobenzoate, butyl 2-chloro-4,5-difluorobenzoate, isobutyl 2-chloro-4,5-difluorobenzoate and 2,2,2-trifluoroethyl 2-chloro-4,5-difluorobenzoate.

The compounds of the formula (3) can readily be prepared by the following reaction:

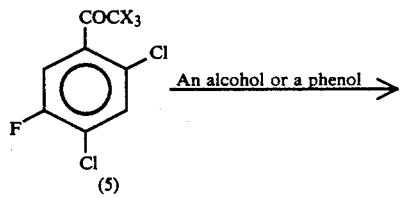

wherein X is a halogen atom, preferably a chlorine atom, and R¹ is an alkyl group, an aryl group or a fluoroalkyl group.

Namely, the compounds of the formula (3) can be prepared by reacting the compounds of the formula (5) i.e. a 2,4-dichloro-5-fluoro-α,α,α-trihalogenoacetophenone with an alcohol or with a phenol. This reaction is preferably conducted in the presence of a base. As such a base, an inorganic salt such as potassium hydrogen carbonate, sodium hydrogen carbonate, potassium carbonate, sodium carbonate or sodium acetate, or an organic base such as pyridine, triethylamine or ethylamine, may be employed. However, the base is not restricted to such specific examples. The base is used usually in an amount of from 0.01 to 2 mols, preferably from 0.1 to 1 mol, per mol of the starting material. The alcohol or the phenol is used usually in an amount of from 1 to 3 mols, pereferably from 1 to 1.5 mols, per mol of the starting material. The reaction temperature is from 0° to 100° C., preferably from 50° to 90° C.

Such fluorine-containing benzoates may also be prepared, for example, by the following reaction.

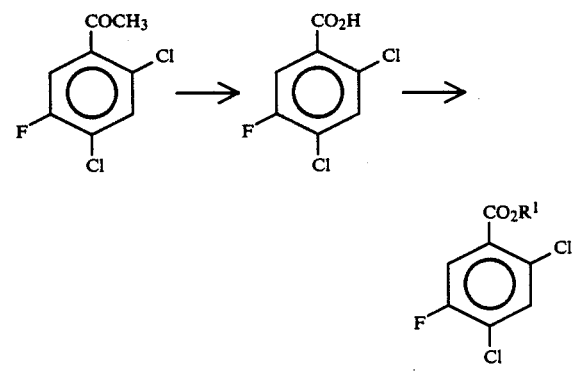

Namely, 2,4-dichloro-5-fluoroacetophenone is subjected to a haloform reaction in a 12% sodium hypophosphite aqueous solution to obtain 2,4-dichloro-5-fluorobenzoic acid. Then, this benzoic acid is reacted with an alcohol or with a phenol in the presence of an acid catalyst to obtain the above-mentioned fluorine-containing benzoate.

Further, such benzoates can be converted to the corresponding benzoic acids by e.g. the following reaction, and further they can be led to quinolone carboxylic acids useful as synthetic antimicrobial agents by known reactions involving a few steps.

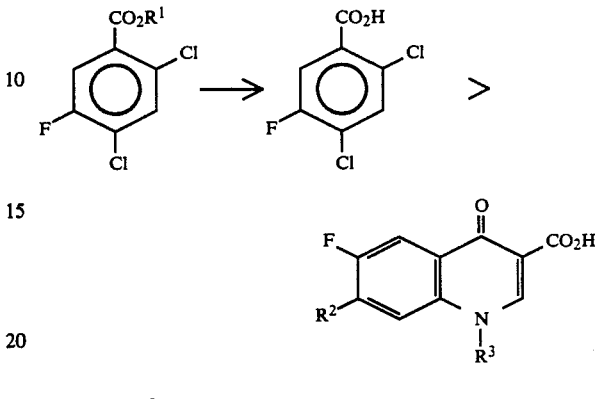

wherein R² is

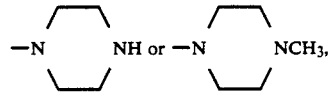

and R³ is preferably

The 2,4-dichloro-5-fluoro-α,α,α-trihalogenoacetophenone of the formula (5) is a novel compound, and it includes, for example, the following compounds:

α,α,α,2,4-pentachloro-5-fluoroacetophenone (X=Cl);
α,α,α-tribromo-2,4-dichloro-5-fluoroacetophenone (X=Br); and
2,4-dichloro-5-fluoro-α,α,α-triiodoacetophoenone (X=I).

The compounds of the formula (5) can readily be prepared by the following reaction:

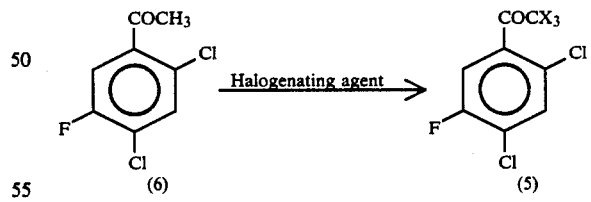

wherein X is a halogen atom.

Namely, the compound of the formula (6) i.e. 2,4-dichloro-5-fluoroacetophenone is simply reacted with a halogenating agent. As such a halogenating agent, chlorine gas, bromine or iodine is preferred. It is used usually in an amount of from 1.5 to 10 mols, preferably from 3 to 6 mols, per mol of the starting material. The reaction temperature is usually from 50° to 250° C., preferably from 100° to 220° C.

2-Chloro-4,5-difluorobenozoate of the following formula (4) can be prepared by reacting 2,4-dichloro-5-fluoroacetophenone of the following formula (6) with a halogenating agent to obtain 2,4-dichloro-5-fluoro-α,α,α-trihalogenoacetophonone of the following formula (5), then reacting the acetophenone of the formula (5) with an alcohol or with a phenol to obtain 2,4-dichloro-5-fluorobenzoate of the following formula (3), and then nucleus-fluorinating the benzoate of the formula (3) with a fluorinating agent:

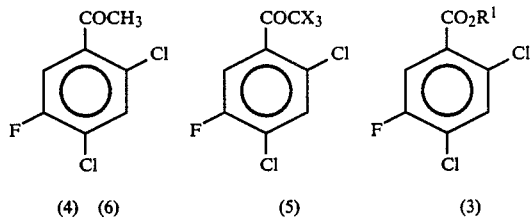

(4) (6)    (5)    (3)

wherein X is a halogen atom, and $R^1$ is an alkyl group, an aryl group or a fluoroalkyl group.

2-Chloro-4,5-difluorobenzoate of the formula (4) can be obtained by reacting 2,4-dichloro-5-fluoro-α,α,α-trihalogenoacetophenone of the formula (5) as the starting material with an alcohol or with a phenol to obtain 2,4-dichloro-5-fluorobenzoate of the formula (3) and then nucleus-fluorinating the benzoates of the formula (3) with a fluorinating agent.

2,4-Dichloro-5-fluorobenzoate of the formula (3) can be prepared by reacting 2,4-dichloro-5-fluoroacetophonone of the formula (6) with a halogenating agent to obtain 2,4-dichloro-5-fluoro-α,α,α-trihalogenoacetophenone of the formula (5), and then reacting the acetophenone of the formula (5) with an alcohol or with a phenol.

Now, the present invention will be described in further detail with reference to Examples. However, it should be understood that the present invention is by no means restricted by such specific Examples.

EXAMPLE 1

Isopropyl 2,4-dichloro-5-fluorobenzoate

To 310.5 g (1 mol) of α,α,α,2,4-pentachloro-5-fluoroacetophenone, 90 g (1.5 mol) of 2-propanol and 13.8 g (0.1 mol) of potassium carbonate were added, and the mixture was reacted at 85° C. for 6 hours. After cooling, the inorganic salt was removed by filtration, and the filtrate was distilled under reduced pressure to obtain 218 g (yield: 87%) of isopropyl 2,4-dichloro-5-fluorobenzoate. This compound was analyzed, and the results are as shown below.

Boiling point: 94° C./3 mmHg
Melting point: 35° C.
NMR analysis <$^{19}$Fnmr> δppm from CFCl$_3$ in CDCl$_3$, δ −117.1 ppm (d,d, $J_{F-H}$=6.5 Hz, $J_{F-H}$=9.0 Hz), <$^1$Hnmr> δppm from TMS in CDCl$_3$, δ 1.39 (6H, d, J=6.3 Hz), δ 5.26 (1H, m), δ 7.50 (1H, d, $J_{H-F}$=6.5 Hz), δ 7.61 (1H, d, $J_{H-F}$=9.0 Hz).
IR analysis 1738 cm$^{-1}$ (C=O).

EXAMPLE 2 n-Propyl 2,4-dichloro-5-fluorobenzoate

By using 90.0 g (1.5 mol) of 1-propanol, the reaction was conducted at 85° C. for 4 hours in the same manner as in Example 1 to obtain 215.9 g (yield: 86%) of n-propyl 2,4-dichloro-5-fluorobenzoate. This compound was analyzed, and the results are as shown below.

NMR analysis <$^{19}$Fnmr> δppm from CFCl$_3$ in CDCl$_3$, δ −117.0 ppm (d,d, $J_{F-H}$=6.4 Hz, $J_{F-H}$=9.0 Hz), <$^1$Hnmr> δppm from TMS in CDCl$_3$, δ 1.04 (3H, t, J=7.4 Hz), δ 1.76 (2H, m), δ 4.30 (2H, t, J=6.6 Hz), δ 7.46 (1H, d, $J_{H-F}$=6.4 Hz), δ 7.63 (1H, d, $J_{H-F}$=9.0 Hz).
IR analysis 1738 cm$^{-1}$ (C=O).

EXAMPLE 3 n-Butyl 2,4-dichloro-5-fluorobenzoate

By using 111.2 g (1.5 mol) of 1-butanol, the reaction was conducted at 98° C. for 4 hours in the same manner as in Example 1 to obtain 235.9 g (yield: 89%) of n-butyl 2,4-dichloro-5-fluorobenzoate. This compound was analyzed, and the results are as follows.

NMR analysis <$^{19}$Fnmr> δppm from CFCl$_3$ in CDCl$_3$, δ −117.2 ppm (d,d, $J_{F-H}$=6.5 Hz, $J_{F-H}$=9.0 Hz), <$^1$Hnmr> δppm from TMS in CDCl$_3$, δ 1.24 ppm (3H, t, J=6.7 Hz), δ 1.28–1.92 ppm (4H, m), δ 4.61 ppm (2H, t, J=6.2 Hz), δ 7.77 ppm (1H, d, $J_{F-H}$=6.5 Hz), δ 7.91 ppm (1H, d, $J_{F-H}$=9.0 Hz).
IR analysis 1739 cm$^{-1}$ (C=O).

EXAMPLE 4

Isobutyl 2,4-dichloro-5-fluorobenzoate

By using 111.2 g (1.5 mol) of 2-butanol, the reaction was conducted at 98° C. for 4 hours in the same manner as in Example 1 to obtain 233.2 g (yield: 88%) of isobutyl 2,4-dichloro-5-fluorobenzoate. This compound was analyzed and the results are as follows.

NMR analysis <$^{19}$Fnmr> δppm from CFCl$_3$ in CDCl$_3$ δ −117.1 ppm (d,d, $J_{F-H}$=6.4 Hz, $J_{F-H}$=9.0 Hz) <$^1$Hnmr> δppm from TMS in CDCl$_3$, δ 1.28 ppm (3H, t, J=7.4 Hz), δ 1.65 ppm (3H, d, J=6.3 Hz), δ 1.98 ppm (2H, m), δ 5.40 ppm (1H, m), δ 7.75 ppm (1H, d, $J_{F-H}$=6.4 Hz), δ 7.91 ppm (1H, d, $J_{F-H}$=9.0 Hz).
IR analysis 1739 cm$^{-1}$ (C=O).

EXAMPLE 5

Cyclohexyl 2,4-dichloro-5-fluorobenzoate

By using 150.2 g (1.5 mol) of cyclohexanol, the reaction was conducted at 100° C. for 6 hours in the same manner as in Example 1 to obtain 256.2 g (yield: 88%) of cyclohexyl 2,4-dichloro-5-fluorobenzoate. This compound was analyzed, and the results are as follows.

NMR analysis <$^{19}$Fnmr> δppm from CFCl$_3$ in CDCl$_3$, δ −117.3 ppm (d,d, $J_{F-H}$=6.5 Hz, $J_{F-H}$=9.0 Hz), <$^1$Hnmr> δppm from TMS in CDCl$_3$, δ 1.32–2.09 ppm (10H, m), δ 5.04 ppm (1H, m), δ 7.51 ppm (1H, d, $J_{H-F}$=6.5 Hz), δ 7.64 ppm (1H, d, $J_{H-F}$=9.0 Hz).
IR analysis 1738 cm$^{-1}$ (C=O).

EXAMPLE 6

2,2,2-Trifluoroethyl-2,4-dichloro-5-fluorobenzoate

By using 150.0 g (1.5 mol) of 2,2,2-trifluoroethanol, the reaction was conducted at 75° C. for 2 hours in the same manner as in Example 1 to obtain 253.1 g (yield: 87%) of 2,2,2-trifluoroethyl-2,4-dichloro-5-fluorobenzoate. This compound was analyzed, and the results are as follows.

NMR analysis <$^{19}$Fnmr> δppm from CFCl$_3$ in CDCl$_3$, δ −116.2 ppm (1F, d,d, $J_{F-H}$=6.5 Hz, $J_{F-H}$=8.9 Hz), δ −74.1 ppm (3F, t, $J_{F-H}$=8.3 Hz), <$^1$Hnmr> δppm from TMS in CDCl$_3$, δ 4.73 ppm (2H, q, $J_{H-F}$=8.3 Hz), δ 7.54 ppm (1H, d, $J_{H-F}$=6.5 Hz), δ 7.71 ppm (1H, d, $J_{H-F}$=8.9 Hz).
IR analysis 1740 cm$^{-1}$ (C=O).

EXAMPLE 7

Isopropyl 2-chloro-4,5-difluorobenzoate

Into a 1 l glass reactor equipped with a condenser, 251.0 g (1 mol) of isopropyl 2,4-dichloro-5-fluorobenzoate, 87 g (1.5 mol) of spray-dried potassium fluoride, 25.1 g of tetramethyl ammonium chloride and 500 g of sulforane were charged and reacted at 150° C. for 9 hours under vigorous stirring. After cooling, the inorganic salt was removed by filtration, and the filtrate was distilled under reduced pressure to obtain 199.8 g (yield: 85.2%) of isopropyl 2-chloro-4,5-difluorobenzoate. This compound was analyzed, and the results are as follows.

Boiling point: 84° C./5 mmHg

NMR analysis <$^{19}$Fnmr> δppm from CFCl$_3$ in CDCl$_3$, δ −130.3 ppm (d,d,d, $J_{F-F}$=20.6 Hz, $J_{F-H}$=10.3 Hz, $J_{F-H}$=8.5 Hz), δ −138.9 ppm (d,d,d, $J_{F-F}$=22.2 Hz, $J_{F-H}$=8.4 Hz, $J_{F-H}$=6.2 Hz), <$^1$Hnmr> δppm from TMS in CDCl$_3$, δ 1.38 ppm (6H, d, J=6.3 Hz), δ 5.26 ppm (1H, m), δ 7.28 ppm (1H, d,d, $J_{H-F}$=8.4 Hz, $J_{H-F}$=6.2 Hz), δ 7.70 ppm (1H, d,d, $J_{H-F}$=10.3 Hz, $J_{H-F}$=8.5 Hz).

IR analysis 1742 cm$^{-1}$ (C=O).

REFERENCE EXAMPLE 1

Methyl 2-chloro-4,5-difluorobenzoate

By using 223 g (1 mol) of methyl 2,4-dichloro-5-fluorobenzoate, the reaction was conducted at 150° C. for 8 hours in the same manner as in Example 7 to obtain 99.1 g (yield: 48.0%) of methyl 2-chloro-4,5-difluorobenzoate. This compound was analyzed, and the results are as follows.

NMR analysis <$^{19}$Fnmr> δ ppm from CFCl$_3$ in CDCl$_3$, δ −129.6 ppm (d,d,d, $J_{F-F}$=20.6 Hz, $J_{F-H}$=10.3 Hz, $J_{F-H}$=8.5 Hz), δ −138.9 ppm (d,d,d, $J_{F-F}$=22.2 Hz, $J_{F-H}$=8.4 Hz, $J_{F-H}$=6.2 Hz), <$^1$Hnmr> δppm from TMS in CDCl$_3$, δ 3.93 ppm (3H, s), δ 7.30 ppm (1H, d,d, $J_{H-F}$=8.4 Hz, $J_{H-F}$=6.2 Hz), δ 7.74 ppm (1H, d,d, $J_{H-F}$=10.3 Hz, $J_{H-F}$=8.5 Hz).

IR analysis 1742 cm$^{-1}$ (C=O).

Reference Example 2

Ethyl 2-chloro-4,5-difluorobenzoate

By using 237 g (1 mol) of ethyl 2,4-dichloro-5-fluorobenzoate, the reaction was conducted at 150° C. for 9 hours in the same manner as in Example 7 to obtain 111.8 g (yield: 50.7%) of ethyl 2-chloro-4,5-difluorobenzoate. This compound was analyzed, and the results are as follows.

NMR analysis <$^{19}$Fnmr>δ ppm from CFCl$_3$ in CDCl$_3$, δ −130.0 ppm (d,d,d, $J_{F-F}$=20.6 Hz, $J_{F-H}$=10.4 Hz, $J_{F-H}$=8.2 Hz), δ −138.8 ppm (d,d,d, $J_{F-F}$=21.8 Hz, $J_{F-H}$=8.4 Hz, $J_{F-H}$=6.4 Hz), <$^1$Hnmr>δ ppm from TMS in CDCl$_3$, δ 1.41 ppm (3H, t, J=7.1 Hz), δ 4.40 ppm (2H, q, J=7.1 Hz), δ 7.29 ppm (1H, d,d, $J_{H-F}$=8.4 Hz, $J_{H-F}$=6.4 Hz), δ 7.73 ppm (1H, d,d, $J_{H-F}$=10.4 Hz, $J_{H-F}$=8.2 Hz).

IR analysis 1742 cm$^{-1}$ (C=O).

EXAMPLE 10 n-Propyl 2-chloro-4,5-difluorobenzoate

By using 251 g (1 mol) of n-propyl 2,4-dichloro-5-fluorobenzoate, the reaction was conducted at 150° C. for 9 hours in the same manner as in Example 7 to obtain 199.8 g (yield: 85.2%) of propyl 2-chloro-4,5-difluorobenzoate. This compound was analyzed, and the results are as follows.

NMR analysis <$^{19}$Fnmr>δ ppm from CFCl$_3$ in CDCl$_3$, δ −130.0 ppm (d,d,d, $J_{F-F}$=20.6 Hz, $J_{F-H}$=10.4 Hz, $J_{F-H}$=8.3 Hz), δ −138.7 ppm (d,d,d, $J_{F-F}$=22.0 Hz, $J_{F-H}$=8.4 Hz, $J_{F-H}$=6.4 Hz), <$^1$Hnmr>δ ppm from TMS in CDCl$_3$, δ 1.04 ppm (3H, t, J=6.9 Hz), δ 1.80 ppm (2H, m), δ 4.30 ppm (2H, t, J=6.6 Hz), δ 7.30 ppm (1H, d,d, $J_{H-F}$=8.4 Hz, $J_{H-F}$=6.4 Hz), δ 7.74 ppm (1H, d,d, $J_{H-F}$=10.4 Hz, $J_{H-F}$=8.3 Hz), IR analysis 1742 cm$^{-1}$ (C=O).

EXAMPLE 11 n-Butyl 2-chloro-4,5-difluorobenzoate

By using 265 g (1 mol) of n-butyl 2,4-dichloro-5-fluorobenzoate, the reaction was conducted at 150° C. for 3 hours in the same manner as in Example 7 to obtain 179.9 g (yield: 72.4%) of n-butyl 2-chloro-4,5-difluorobenzoate. This compound was analyzed, and the results are as follows.

NMR analysis <$^{19}$Fnmr> 67 ppm from CFCl$_3$ in CDCl$_3$, δ −130.0 ppm (d,d,d, $J_{F-F}$=20.6 Hz, $J_{F-H}$=10.5 Hz, $J_{F-H}$=8.4 Hz), δ −138.7 ppm (d,d,d, $J_{F-F}$=21.8 Hz, $J_{F-H}$=8.4 Hz, $J_{F-H}$=6.2 Hz), <$^1$Hnmr> δppm from TMS in CDCl$_3$, δ 0.98 ppm (3H, t, J=6.5 Hz), δ 1.28–1.93 ppm (4H, m), δ 4.34 ppm (2H, t, J=6.4 Hz), δ 7.29 ppm (1H, d,d, $J_{H-F}$=8.4 Hz, $J_{H-F}$=6.2 Hz), δ 7.7 ppm (1H, d,d, $J_{H-F}$=10.5 Hz, $J_{H-F}$=8.4 Hz).

IR analysis 1742 cm$^{-1}$ (C=O).

EXAMPLE 12

Isobutyl 2-chloro-4,5-difluorobenzoate

By using 265 g (1 mol) of isobutyl 2,4-dichloro-5-fluorobenzoate, the reaction was conducted at 150° C. for 3 hours in the same manner as in Example 7 to obtain 194.8 g (yield: 78.4%) of isobutyl 2-chloro-4,5-difluorobenzoate. This compound was analyzed and the results are as follows.

NMR analysis <$^{19}$Fnmr> δppm from CFCl$_3$ in CDCl$_3$, δ 130.3 ppm (d,d,d, $J_{F-F}$=20.8 Hz, $J_{F-H}$=10.4 Hz, $J_{F-H}$=8.4 Hz), δ 138.8 ppm (d,d,d, $J_{F-F}$=21.8 Hz, $J_{F-H}$=8.4 Hz, $J_{F-H}$=6.4 Hz), <$^1$Hnmr> δppm from TMS in CDCl$_3$, δ 0.99 ppm (3H, t, J=7.0 Hz), δ 1.35–1.93 ppm (3H, d, J=6.3 Hz), δ 1.87 ppm (2H, m), δ 5.11 ppm (1H, m), δ 7.28 ppm (1H, d,d, $J_{H-F}$=8.4 Hz, $J_{H-F}$=6.4 Hz), δ 7.71 ppm (1H, d,d, $J_{H-F}$=10.4 Hz, $J_{H-F}$=8.4 Hz).

IR analysis 1742 cm$^{-1}$ (C=O).

EXAMPLE 13

2,2,2-Trifluoroethyl-2-chloro-4,5-difluorobenzoate

By using 291 g (1 mol) of 2,2,2-trifluoroethyl 2,4-dichloro-5-fluorobenzoate, the reaction was conducted at 150° C. for 4 hours in the same manner as in Example 7 to obtain 256.2 g (yield: 83.3%) of 2,2,2-trifluoroethyl 2-chloro-4,5-difluorobenzoate.

Boiling point: 106° C./16 mmHg

NMR analysis <$^{19}$Fnmr> δppm from CFCl$_3$ in CDCl$_3$, δ 127.6 ppm (1F, d,d,d, $J_{F-F}$=20.6 Hz, $J_{F-H}$=10.2 Hz, $J_{F-H}$=8.2 Hz), δ 137.7 ppm (1F, d,d,d, $J_{F-F}$=21.8 Hz, $J_{F-H}$=8.4 Hz, $J_{F-H}$=6.2 Hz), δ 74.1 ppm (3F, t, $J_{F-H}$=8.32 Hz), <$^1$Hnmr> δppm from TMS in CDCl$_3$, δ 4.71 ppm (2H, q, $J_{H-F}$=8.3 Hz), δ 7.35 ppm (1H, d,d, $J_{H-F}$=8.4 Hz, $J_{H-F}$=6.2 Hz), δ 7.70 ppm (1H, d,d, $J_{H-F}$=10.2 Hz, $J_{H-F}$=8.2 Hz).

IR analysis 1740 cm$^{-1}$ (C=O).

EXAMPLE 14

α,α,α,2,4-pentachloro-5-fluoroacetophenone

Into a 500 ml glass reactor equipped with a condenser and a gas supply tube, 207 g (1 mol) of 2,4-dichloro-5-fluoroacetophenone was charged. While the reaction temperature was gradually raised from 120° C. to 200° C., 426 g (6 mol) of chlorine gas was blown into the reactor over a period of 20 hours under atmospheric pressure. After cooling, the reaction mixture was washed with water, with a 5% potassium hydrogen carbonate aqueous solution and then with water, followed by drying and distillation under reduced pressure to obtain 298 g (yield: 96%) of α,α,α,2,4-pentachloro-5-fluoroacetophenone.

This compound was analyzed, and the results are as follows.

Boiling point: 110° C./2.5 mmHg

NMR analysis $<^{19}Fnmr>$ δppm from $CFCl_3$ in $CDCl_3$, δ 115.6 ppm (d,d, $J_{F-H}$=6.6 Hz, $J_{F-H}$=8.2 Hz), $<^{1}Hnmr>$ δppm from TMS in $CDCl_3$, δ 7.58 ppm (1H, d, $J_{H-F}$=6.6 Hz), δ 7.62 ppm (1H, d, $J_{H-F}$=8.2 Hz).

IR analysis 1740 $cm^{-1}$ (C=O).

EXAMPLE 15

2,2,2-Trifluoroethyl 2-chloro-4,5-difluorobenzoate

Into a 1 l glass reactor equipped with a condenser, 291 g (1 mol) of 2,2,2-trifluoroethyl 2,4-dichloro-5-fluorobenzoate, 87 g (1.5 mol) of spray dried potassium fluoride and 500 g of sulforane were charged and reacted at 180° C. for 9 hours under vigorous stirring. After cooling, the inorganic salt was removed by filtration, and the filtrate was distilled under reduced pressure to obtain 239.4 g (yield: 87.2%) of 2,2,2-trifluoroethyl 2-chloro-4,5-difluorobenzoate.

EXAMPLE 16

2,2,2-Trifluoroethyl-2,4,5-trifluorobenzoate

By using 291 g (1 mol) of 2,2,2-trifluoroethyl 2,4-dichloro-5-fluorobenzoate, the reaction was conducted at 180° C. for 32 hours in the same manner as in Example 15 to obtain 158.7 g (yield: 65.5%) of 2,2,2-trifluoroethyl 2,4,5-trifluorobenzoate.

EXAMPLE 17

2,2,2-Trifluoroethyl 2-fluorobenzoate

By using 238.5 g (1 mol) of 2,2,2-trifluoroethyl 2'-chlorobenzoate, the reaction was conducted at 180° C. for 18 hours in the same manner as in Example 15 to obtain 179.2 g (yield: 80.7%) of 2,2,2-trifluoroethyl 2-fluorobenzoate.

EXAMPLE 18

2,2,2-Trifluoroethyl 4-fluorobenzoate

By using 238.5 g (1 mol) of 2,2,2-trifluoroethyl 4'-chlorobenzoate, the reaction was conducted at 180° C. for 10 hours in the same manner as in Example 15 to obtain 183.2 g (yield: 82.5%) of 2,2,2-trifluoroethyl 4-fluorobenzoate.

EXAMPLE 19

2,2,2-Trifluoroethyl 2,4-difluorobenzoate

By using 273.5 g (1 mol) of 2,2,2-trifluoroethyl 2,4-dichlorobenzoate, the reaction was conducted at 180° C. for 15 hours in the same manner as in Example 15 to obtain 191.5 g (yield: 79.8%) of 2,2,2-trifluoroethyl 2,4-difluorobenzoate.

EXAMPLE 20

2,2,2-Trifluoroethyl 2,6-difluorobenzoate

By using 273.5 g (1 mol) of 2,2,2-trifluoroethyl 2,6-dichlorobenzoate, the reaction was conducted at 180° C. for 20 hours in the same manner as in Example 15 to obtain 175.9 g (yield: 73.3%) of 2,2,2-trifluoroethyl 2,6-difluorobenzoate.

EXAMPLE 21

2,2,2-Trifluoroethyl 3-chloro-4,5-difluorobenzoate

By using 307.5 g (1 mol) of 2,2,2-trifluoroethyl 3,4,5-trichlorobenzoate, the reaction was conducted at 180° C. for 10 hours in the same manner as in Example 15 to obtain 179.5 g (yield: 65.4%) of 2,2,2-trifluoroethyl 3-chloro-4,5-difluorobenzoate.

EXAMPLE 22

2,2,2-Trifluoroethyl 3,4,5-trifluorobenzoate

By using 307.5 g (1 mol) of 2,2,2-trifluoroethyl 3',4',5'-trichlorobenzoate, the reaction was conducted at 180° C. for 30 hours in the same manner as in Example 15 to obtain 97.7 g (yield: 35.6%) of 2,2,2-trifluoroethyl 3,4,5-trifluorobenzoate.

EXAMPLE 23

1-Trifluoromethyl-2,2,2-trifluoroethyl 2'-chloro-4',5'-difluroobenzoate

By using 359.0 g (1 mol) of 1-trifluoromehtyl-2,2,2-trifluoroethyl 2,4-dichloro-5-fluorobenzoate, the reaction was conducted at 180° C. for 8 hours in the same manner as in Example 15 to obtain 290.4 g (yield: 84.8%) of 1-trifluoromethyl-2,2,2-trifluoroethyl 2-chloro-4,5-difluorobenzoate.

EXAMPLE 24

2,2,3,3,3-Pentafluoropropyl 2-chloro-4,5-difluorobenzoate

By using 341.0 g (1 mol) of 2,2,3,3,3-pentafluoropropyl 2,4-dichloro-5-fluorobenzoate, the reaction was conducted at 180° C. for 8 hours in the same manner as in Example 15 to obtain 276.1 g (yield: 85.1%) of 2,2,3,3,3-pentafluoropropyl 2-chloro-4,5-difluorobenzoate.

EXAMPLE 25

2,2,2-Trifluoroethyl 2-fluorobenzoate

Into a 1 l glass reactor equipped with a condenser, 238.5 g (1 mol) of 2,2,2-trifluoroethyl 2-chlorobenzoate, 87 g (1.5 mol) of spray dried potassium fluoride, 23.9 g of tetrabutyl phosphonium bromide and 480 g of sulforane were charged and reacted at 180° C. for 20 hours under vigorous stirring. After cooling, the inorganic salt was removed by filtration, and the filtrate was distilled under reduced pressure to obtain 134.3 g (yield: 60.5%) of 2,2,2-trifluoroethyl 2-fluorobenzoate.

EXAMPLE 26

Isopropyl 4-fluorobenzoate

By using 198.5 g (1 mol) of isopropyl 4-chlorobenzoate and 19.9 g of tetramethyl ammonium chloride, the reaction was conducted at 180° C. for 15 hours in the same manner as in Example 25 to obtain 147.8 g (81.7%) of isopropyl 4-fluorobenzoate.

EXAMPLE 27

Isopropyl 2-chloro-4-fluorobenzoate

By using 233 g (1 mol) of isopropyl 2,4-dichlorobenzoate, the reaction was conducted at 150° C. for 14 hours in the same manner as in Example 26 to obtain 173.4 g (yield: 80.1%) of isopropyl 2-chloro-4-fluorobenzoate.

EXAMPLE 28

2,2,2-Trifluoroethyl 2,4-difluorobenzoate

By using 273 g (1 mol) of 2,2,2-trifluoroethyl 2,4-dichlorobenzoate, the reaction was conducted at 200° C. for 20 hours in the same manner as in Example 25 to obtain 139.8 g (yield: 58.3%) of 2,2,2-trifluoroethyl 2,4-difluorobenzoate.

EXAMPLE 29

2,2,2-Trifluoroethyl 2,6-difluorobenzoate

By using 273 g (1 mol) of 2,2,2-trifluoroethyl 2,6-dichlorobenzoate, the reaction was conducted at 200° C. for 30 hours in the same manner as in Example 25 to obtain 138.2 g (yield: 57.6%) of 2,2,2-trifluoroethyl 2,6-difluorobenzoate.

Reference Example 3

Methyl 2-chloro-4,5-difluorobenzoate

By using 223 g (1 mol) of methyl 2,4-dichloro-5-fluorobenzoate, the reaction was conducted at 150° C. for 8 hours in the same manner as in Example 26 to obtain 99.1 g (yield: 48.0%) of methyl 2-chloro-4,5-difluorobenzoate.

Reference Example 4

Ethyl 2-chloro-4,5-difluorobenzoate

By using 237 g (1 mol) of ethyl 2,4-dichloro-5-fluorobenzoate, the reaction was conducted at 150° C. for 9 hours in the same manner as in Example 26 to obtain 111.8 g (yield: 50.7%) of ethyl 2-chloro-4,5-difluorobenzoate.

EXAMPLE 32

Isopropyl 2-chloro-4,5-difluorobenzoate

By using 251 g (1 mol) of isopropyl 2,4-dichloro-5-fluorobenzoate, the reaction was conducted at 150° C. for 9 hours in the same manner as in Example 26 to obtain 199.8 g (yield: 85.2%) of isopropyl 2-chloro-4,5-difluorobenzoate.

EXAMPLE 33

Phenyl 2-chloro-4,5-difluorobenzoate

By using 285 g (1 mol) of phenyl 2,4-dichloro-5-fluorobenzoate, the reaction was conducted at 150° C. for 3 hours in the same manner as in Example 16 to obtain 194.5 g (yield: 72.4%) of phenyl 2-chloro-4,5-difluorobenzoate.

EXAMPLE 34

2,2,2-Trifluoroethyl 2,4,5-trifluorobenzoate

By using 291 g (1 mol) of 2,2,2-trifluoroethyl 2,4-dichloro-5-fluorobenzoate, the reaction was conducted at 200° C. for 30 hours in the same manner as in Example 25 to obtain 126.2 g (yield: 48.2%) of 2,2,2-trifluoroethyl 2,4,5-trifluorobenzoate.

EXAMPLE 35

Bis(2,2,2-trifluoroethyl) tetrafluorophthalate

By using 234 g (0.5 mol) of bis(2,2,2-trifluoroethyl) tetrachlorophthalate, the reaction was conducted at 200° C. for 30 hours in the same manner as in Example 25 to obtain 104.5 g (yield: 52.0%) of bis(2,2,2-trifluoroethyl) tetrafluorophthalate.

According to the present invention, the desired nucleus-fluorinated aromatic carboxylate can be obtained on an industrial scale at a low cost and in good yield from a readily available aromatic carboxylate.

Further, by changing the alkyl (or aryl) moiety of the alkoxycarbonyl (or aryloxycarbonyl) group of the starting material aromatic carboxylate, it is possible to substitute fluorine for only the halogen at p-position or both halogens at the o- and p-positions to the alkoxycarbonyl (or aryloxycarbonyl) group. Thus, the process of the present invention is very useful.

We claim:

1. A process for producing nucleus-fluorinated aromatic carboxylates, which comprise nucleus-fluorinating aromatic carboxylates of the following formula (1) with a fluorinating agent comprising an alkali metal fluoride in an amount of from 1 to 5 mols per mole of halogen atom to be substituted, at a temperature of from 50° to 250° C., to obtain nucleus-fluorinated aromatic carboxylates of the following formula (2):

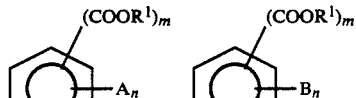

(1)      (2)

wherein $R^1$ is an alkyl group, an aryl group or a fluoroalkyl group, each of A and B is at least one member selected from the group consisting of a hydrogen atom, a halogen atom, an alkyl group, an aryl group and a fluoroalkyl group, and n and m are integers satisfying $m+n=6$, provided that m is 1 or 2, provided that at least one A is an activated chlorine or bromine atom, and B corresponding to such an activated chlorine or bromine atom is a fluorine atom.

2. The process according to claim 1, wherein the activated chlorine or bromine atom is a chlorine or bromine atom located at the o- or p-position to the —$COOR^1$ groups.

3. The process according to claim 1, wherein the fluorinating agent is potassium fluoride.

4. A process for producing 2-chloro-4,5-difluorobenzoates, which comprises nucleus-fluorinating 2,4-dichloro-5-fluorobenzoates of the following formula (3) with a fluorinating agent comprising an alkali metal fluoride in an amount of from 1 to 5 mols per mole of halogen atom to be substituted, at a temperature of from 50° to 250° C., to obtain 2-chloro-4,5-dichlorofluorobenzoates of the following formula (4):

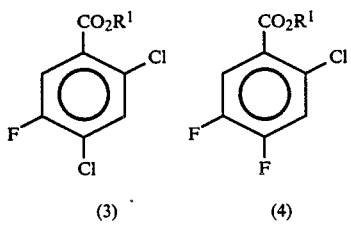

(3)   (4)

wherein R¹ is an alkyl group, an aryl group or a fluoroalkyl group.

5. The process according to claim 4, wherein the fluorinating agent is potassium fluoride.

6. A process for producing 2,4-dichloro-5-fluorobenzoates, which comprises reacting 2,4-dichloro-5-fluoro-α,α,α-trihalogenoacetophenones of the following formula (5) with an alcohol or with a phenol to obtain 2,4-dichloro-5-fluorobenzoates of the following formula (3):

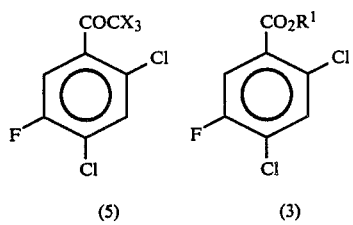

(5)   (3)

wherein X is a halogen atom, and R¹ is an alkyl group, an aryl group or a fluoroalkyl group.

7. The process according to claim 6, wherein X in the formula (5) is a chlorine atom.

8. A process for producing 2,4-dichloro-5-fluoro-α,α,α-trihalogenoacetophenones, which comprises reacting 2,4-dichloro-5-fluoroacetophenone of the formula (6) with a halogenating agent to obtain 2,4-dichloro-5-dichloro-5-fluoro-α,α,α-trihalogenoacetophenones of the following formula (5):

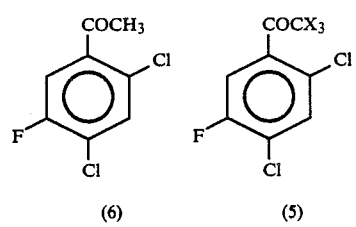

(6)   (5)

wherein X is a halogen atom.

9. The process according to claim 8, wherein X in the formula (5) is a chlorine atom.

10. The process according to claim 8, wherein the halogenating agent is chlorine gas.

11. A process for producing 2-chloro-4,5-difluorobenzoates, which comprises reacting 2,4-dichloro-5-fluoroacetophenone of the following formula (6) with a halogenating agent to obtain 2,4-dichloro-5-fluoro-α,α,α-trihalogenoacetophenones of the following formula (5), then reacting the acetophenones of the formula (5) with an alcohol or with a phenol to obtain 2,4-dichloro-5-fluorobenzoates of the following formula (3), and then nucleus-fluorinating the benzoates of the formula (3) with a fluorinating agent comprising an alkali metal fluoride in an amount of from 1 to 5 mols per mole of halogen atom to be substituted, at a temperature of from 50° to 250° C., to obtain 2-chloro-4,5-difluorobenzoates of the following formula (4):

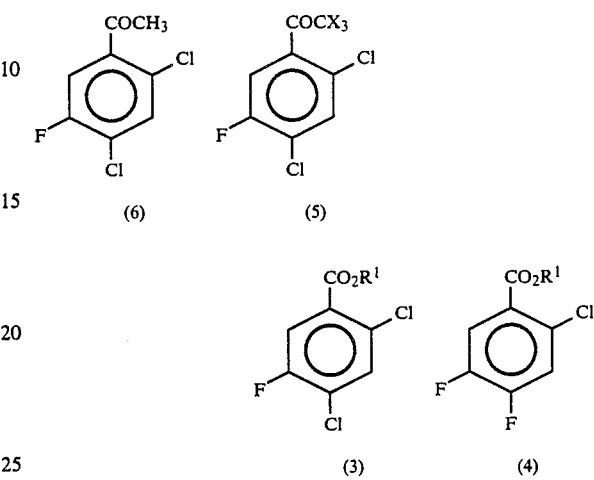

(6)   (5)

(3)   (4)

wherein X is a halogen atom, and R' is an alkyl group, an aryl group or a fluoroalkyl group.

12. A process for producing 2-dichloro-4,5-difluorobenzoates, which comprise reacting 2,4-dichloro-5-fluoro-α,α,α-trihalogenoacetophenones of the following formula (5) with an alcohol or with a phenol to obtain 2,4-dichloro-5-fluorobenzoates of the following formula (3), with a fluorinating agent comprising an alkali metal fluoride in an amount of from 1 to 5 mols per mole of halogen atom to be substituted, at a temperature of from 50° to 250° C., to obtain 2-chloro-4,5-difluorobenzoates of the following formula (4):

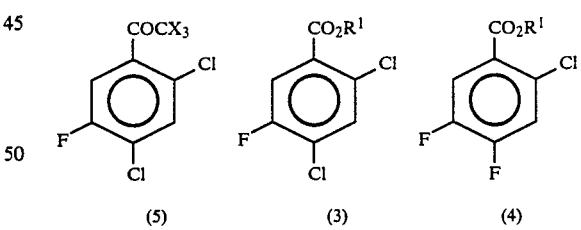

(5)   (3)   (4)

wherein X is a halogen atom, and R¹ is an alkyl group, an aryl group or a fluoroalkyl group.

13. A process for producing 2,4-dichloro-5-fluorobenzoates, which comprises reacting 2,4-dichloro-5-fluorobacetophenone of the following formula (6) with a halogenating agent to obtain 2,4-dichloro-5-fluoro-α,α,α-trihalogenoacetophenones of the following formula (5), and then reacting the acetophenones of the formula (5) with an alcohol or with a phenol to obtain 2,4-dichloro-5-fluorobenzoates of the following formula (3):

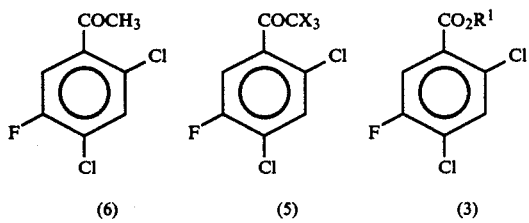

(6)   (5)   (3)

wherein X is a halogen atom, and R¹ is an alkyl group, an aryl group or a fluoroalkyl group.

14. 2,4-Dichloro-5-fluorobenzoates of the formula (3):

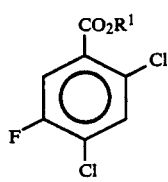

(3)

wherein R¹ is an alkyl group selected from the group consisting of isopropyl, n-propyl, n-butyl, isobutyl and cyclohexyl; an aryl group; or a fluoroalkyl group.

15. 2-Chloro-4,5-difluorobenzoates of the formula (4):

(4)

wherein R¹ is an alkyl group, an aryl group or a fluoroalkyl group.

16. 2-Chloro-4,5-difluorobenzoates according to claim 15, wherein R¹ in the formula (4) is a member selected from the group consisting of methyl, ethyl, n-propyl, isopropyl, n-butyl, isobutyl and trifluoroethyl.

17. 2,4-Dichloro-5-fluoro-α,α,α-trihalogenoacetophenones of the formula (5):

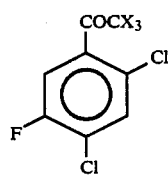

(5)

wherein X is a halogen atom.

18. 2,4-Dichloro-5-fluoro-α,α,α-trihalogenoacetophenones according to claim 17, wherein X in the formula (5) is a chlorine atom.

* * * * *